United States Patent
Liu et al.

(10) Patent No.: US 8,486,862 B2
(45) Date of Patent: Jul. 16, 2013

(54) COMPOSITIONS AND METHODS FOR IMPROVING THE COMPATIBILITY OF WATER SOLUBLE HERBICIDE SALTS

(75) Inventors: Lei Liu, Carmel, IN (US); Hong Zhang, Carmel, IN (US); Alex Kennedy, Fishers, IN (US); Holger Tank, Zionsville, IN (US); Mei Li, Westfield, IN (US); Kuide Qin, Westfield, IN (US); David G. Ouse, Indianapolis, IN (US); Stephen L. Wilson, Zionsville, IN (US); Brandon Matthew Downer, Lebanon, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/215,748

(22) Filed: Aug. 23, 2011

(65) Prior Publication Data

US 2012/0053056 A1    Mar. 1, 2012

Related U.S. Application Data

(60) Provisional application No. 61/376,360, filed on Aug. 24, 2010.

(51) Int. Cl.
*A01N 57/00* (2006.01)
(52) U.S. Cl.
USPC .......................................................... 504/127

(58) Field of Classification Search
None
See application file for complete search history.

(56) References Cited

U.S. PATENT DOCUMENTS

| | | | |
|---|---|---|---|
| 2006/0019828 A1* | 1/2006 | Becher et al. | 504/116.1 |
| 2006/0040828 A1* | 2/2006 | Mao et al. | 504/365 |

FOREIGN PATENT DOCUMENTS

| | | |
|---|---|---|
| WO | WO2006/127501 A2 | 11/2006 |
| WO | WO2007/147208 A1 | 12/2007 |
| WO | WO2008/069826 A1 | 6/2008 |
| WO | WO2011/019652 A2 | 2/2011 |
| WO | WO/2012/027349 | 3/2012 |

OTHER PUBLICATIONS

Technical Bulletin: Lupasol G20 Polyethylenimine. BASF, The Chemical Company, 2010. www.performance.basf-corp.com.
Lupasol Product Range. BASF, Sep. 1996.

* cited by examiner

*Primary Examiner* — Alton Pryor
(74) *Attorney, Agent, or Firm* — Michael R. Asam

(57) ABSTRACT

The compatibility of aqueous herbicide solutions containing water soluble salts of 2,4-D and glyphosate in the presence of inorganic cations is improved by the addition of polyethylenimine or polyvinylamine crystallization inhibitors.

10 Claims, No Drawings

COMPOSITIONS AND METHODS FOR IMPROVING THE COMPATIBILITY OF WATER SOLUBLE HERBICIDE SALTS

CROSS REFERENCE TO RELATED APPLICATIONS

This application claims the benefit of U.S. Provisional Patent Application Ser. No. 61/376,360 filed Aug. 24, 2010.

FIELD OF THE INVENTION

This invention relates to compositions and methods for improving the compatibility of aqueous solutions of water soluble salts of the herbicides 2,4-dichlorophenoxyacetic acid (2,4-D) and glyphosate in the presence of inorganic cations.

BACKGROUND OF THE INVENTION

Aqueous concentrate formulations of pesticidal and plant growth modifying chemicals are widely used in agricultural, industrial, recreational and residential areas worldwide. The active ingredients of such concentrates frequently contain acid functional groups such as carboxylic or phosphonic acids, more commonly in the form of their water soluble salts. An aqueous concentrate is essentially a solution of the active ingredient in water at relatively high concentration, intended for dilution in water prior to application by spraying or other means. Typically the aqueous concentrate is diluted in about 10 to about 500 times its own volume of water prior to application.

2,4-D and glyphosate (N-(phosphonomethyl)glycine) are members of the phenoxyacetic acid and organophosphonic acid classes of herbicides, respectively. They have limited solubility in water in their acid forms and therefore must be converted into water-soluble salts in order to be formulated as soluble aqueous concentrates. Salts of these herbicidal acids commonly used for preparing these aqueous herbicide concentrates include organo ammonium cations such as, for example, isopropyl ammonium, dimethyl ammonium, triethyl ammonium, monoethanol ammonium, diethanol ammonium, triethanol ammonium, triisopropanol ammonium and N,N,N-trimethylethanol ammonium (choline). In addition, glyphosate is often formulated in an aqueous concentrate as the sesquisodium salt, the mono-potassium salt or the mono- or di-ammonium salt.

In today's agrochemical market with the continued demand for improved productivity it becomes increasingly common to combine more than one formulated product in a spray tank in order to achieve the optimal spectrum of control, efficacy, and delivery efficiency of the products. In doing this, however, spray tank incompatibilities between products can occur at times leading to product performance issues and difficulty in the field application of the products.

Spray tank incompatibility occurs when components of an aqueous pesticide spray tank mixture or solution chemically or physically interact thereby reducing the effectiveness of the spray applied product. The incompatibility of a pesticide spray tank mixture or solution may physically manifest itself through the formation of crystalline precipitates, surface scum, oily droplets, gels, excessive foam or clumps of solid matter, and may result in clogged spray nozzles or screens.

Compatible aqueous pesticide mixtures or solutions are defined as those mixtures or solutions that, when formed by the combination or mixing of one or more pesticide products and/or other commonly used ingredients, result in little or no solids precipitation or phase separation and the retention of their full biological efficacy.

It is well known that aqueous solutions of salts of 2,4-D can have compatibility issues leading to the formation of precipitated solids under the following combination of conditions: (1) a 2,4-D acid equivalent (ae) concentration of about 0.3 weight percent or higher, (2) a pH of about 6 or lower, and (3) the presence of inorganic cations such as, for example, $K^+$, $Na^+$, $Ca^{2+}$, $Mg^{2+}$, $NH_4^+$, $Fe^{2+}$, $Fe^{3+}$ and the like. The exact conditions necessary for the on-set of the crystallization of solids from these solutions of 2,4-D salts will also depend on the temperature and hardness of the water used, pH of the mixture and the actual composition and concentrations of the components in the solution. For example, a spray tank mixture made from concentrates of DMA-6® herbicide (registered trademark of Dow AgroSciences LLC; 2,4-D dimethyl ammonium salt solution with a pH value of about 7) at a rate of 800 g ae/hectare and Roundup WeatherMax® herbicide (registered trademark of Monsanto; glyphosate potassium salt solution with a pH value of about 4.7) at 840 g ae/hectare and a spray volume of about 47 liters/hectare would have a pH value of about 5 and will be incompatible and result in the significant formation of solids.

The common practice of adding ammonium sulfate to aqueous herbicide spray mixtures containing glyphosate to improve herbicide performance may also lead to compatibility problems. If an herbicide such as 2,4-D dimethyl ammonium (DMA) is present in a spray mixture containing glyphosate to which ammonium sulfate has been added, crystallization of solids will occur if the pH and the 2,4-D concentration are in the critical ranges discussed herein.

A number of solutions to the spray tank compatibility issues discussed herein have been proposed and are disclosed, for example, in WO 2006/127501A2, WO 2007/147208A1 and WO 2008/069826A1. These proposed solutions involve the use of additives such as, for example, surfactant based compatibility agents that inhibit the formation of solids or the use of greater than about 10% molar excesses of organic amines, with respect to 2,4-D, to modify the pH of the spray solution and thereby improve spray tank compatibility.

Considering the wide use of glyphosate and 2,4-D aqueous herbicide concentrates, and the development and expected commercial introduction of crops tolerant to both glyphosate and 2,4-D products, there is an increasing need for herbicide formulations of these two herbicidal active ingredients that are compatible when tank mixed together and used under a wide range of field conditions.

The present invention provides a novel solution to the compatibility problems encountered between aqueous solutions of water soluble salts of 2,4-D and glyphosate in the presence of inorganic cations.

SUMMARY OF THE INVENTION

The present invention concerns a method of improving the compatibility of aqueous herbicide solutions containing a water soluble salt of 2,4-D and a water soluble salt of glyphosate, wherein such solutions contain one or more inorganic cations selected from the group consisting of $NH_4^+$, $Na^+$, $K^+$, $Ca^{2+}$, $Mg^{2+}$, $Fe^{2+}$, $Fe^{3+}$, $Cu^{2+}$, $Mn^{2+}$ and $Zn^{2+}$, which comprises adding to the aqueous herbicide solution one or more polyethylenimine or polyvinylamine crystallization inhibitors. The aqueous herbicide solutions show improved compatibility without having to increase the pH level, particularly in the presence of additional inorganic cations.

Another embodiment of the present invention concerns an aqueous herbicide solution of improved compatibility comprising a water soluble salt of 2,4-D or glyphosate, or a pre-mix containing water soluble salts of both 2,4-D and glyphosate, and one or more polyethylenimine or polyvinylamine crystallization inhibitors. The aqueous herbicide solutions may be either a concentrate or a spray solution prepared by either diluting such a concentrate or tank-mixing the components of the spray solution.

Another embodiment of the present invention concerns a dry herbicide composition containing one or more polyethylenimine or polyvinylamine crystallization inhibitors, a water soluble salt of 2,4-D or glyphosate, or a mixture of water soluble salts of 2,4-D and glyphosate.

A further embodiment of the present invention concerns a method of using the aqueous herbicidal spray solution of improved compatibility for agricultural spray applications such as for the control of undesired plant growth.

DETAILED DESCRIPTION OF THE INVENTION

It has now been found that the use of relatively small amounts of polyethylenimine or polyvinylamine crystallization inhibitors in aqueous solutions containing soluble salts of 2,4-D and glyphosate will result in the formation of solutions of improved compatibility in the presence of inorganic cations without the need to raise the pH of the solution.

The present invention concerns an aqueous herbicide solution of improved compatibility which is comprised of a water soluble salt of 2,4-D or glyphosate, or a pre-mix containing water soluble salts of both 2,4-D and glyphosate, and one or more polyethylenimine or polyvinylamine crystallization inhibitors.

The water soluble salts of 2,4-D include those containing an organo ammonium cation such as, but not limited to, isopropyl ammonium, dimethyl ammonium, diethyl ammonium, triethyl ammonium, diethanol ammonium, triethanol ammonium, triisopropanol ammonium and N,N,N-trimethylethanol ammonium (choline). Aqueous solutions containing the water soluble salts of 2,4-D may include herbicidal spray solutions or herbicide concentrates.

The water soluble salts of glyphosate include those salts where the cation is selected from potassium, sodium and ammonium, also organo ammonium such as, for example, isopropyl ammonium, dimethyl ammonium, triethyl ammonium, monoethanol ammonium, diethanol ammonium, triethanol ammonium, choline and the like, and trimethylsulfonium cation and mixtures thereof.

The inorganic cations as described herein are those that when present in appreciable amounts or concentrations may cause aqueous solutions of water soluble salts of 2,4-D and glyphosate to become incompatible and form solids. The inorganic cations may be selected from, for example, the alkali metal cations, such as sodium and potassium, the alkaline earth metal cations, such as calcium and magnesium, the transition metal cations, such as manganese, copper, zinc and iron and, furthermore, ammonium. Aqueous solutions containing water soluble salts of 2,4-D and glyphosate at pH levels below about pH 6.5 tend to be more incompatible in the presence of appreciable concentrations of inorganic cations than are such solutions at higher pH levels.

The term "appreciable concentration of inorganic cations" as used herein refers to the concentration of inorganic cations present in an aqueous solution containing soluble salts of 2,4-D and glyphosate that will lead to the precipitation of solids from that solution if all of the other conditions necessary for incompatibility of the solution exist such as the composition and concentration of the 2,4-D and glyphosate salts, and the temperature, hardness and pH of the water. For example, a concentration of glyphosate potassium of about 0.8 weight percent (wt %) on an acid equivalent (ae) basis or higher in an aqueous solution at room temperature containing greater than about 0.8 wt % of 2,4-D DMA on an ae basis and made with water with a hardness of 342 parts per million (ppm) and a pH of about 5 will be incompatible. The compatibility of such an herbicide solution will depend, in addition to the other factors discussed herein, on the total concentration and actual composition of the inorganic cations present in the solution.

Ingredients that may contribute inorganic cations to the aqueous herbicide solutions discussed herein may include, but are not limited to, products or aqueous solutions containing fertilizers, micronutrients, hard water, co-formulation ingredients and the like, as well as, water soluble salts of glyphosate containing inorganic cations such as, for example, potassium, sodium and ammonium.

Fertilizers may be dispersed or dissolved in water and may contain inorganic cations such as, for example, ammonium and potassium, in sufficient amounts so as to cause incompatibility problems when mixed with an aqueous solution containing the soluble salts of 2,4-D and glyphosate. Fertilizers may include, but are not limited to, ammonium sulfate (AMS), ammonium phosphate, ammonium nitrate, solutions of ammonium nitrate and urea which are commonly referred to in the art as 28% N or UAN, potassium nitrate, potassium phosphate, potassium chloride, potassium carbonate and the like, and mixtures thereof. Preferred fertilizers include AMS and UAN which are commonly used as spray adjuvants or water conditioning agents with glyphosate herbicide treatments in order to improve their efficacy. AMS is commonly used as a spray adjuvant at a concentration of from about 1 to about 5 weight percent with respect to the total spray solution containing the water soluble salt of glyphosate.

Micronutrients may include one or more nutrients essential to plant growth and health that are only needed in very small quantities and may contain, among other things, one or more inorganic cations such as, for example, the cations of manganese, copper, iron, molybdenum and zinc. The micronutrients may be added to aqueous herbicide spray solutions containing water soluble salts of 2,4-D and glyphosate for economical delivery to crop plants. Compatibility problems of these aqueous herbicide spray solutions may occur if the conditions for incompatibility of these solutions exist as described herein.

Co-formulation ingredients include those products or ingredients that contain inorganic cations and may be selected from one or more of adjuvants, antifoam agents, antimicrobial agents, buffering agents, corrosion inhibitors, defoaming agents, deposition agents, dispersants, drift control agents, dyes, freezing point depressants, neutralizing agents, penetration aids, sequestering agents, spreading agents, stabilizers, sticking agents, suspension aids, viscosity-modifying additives, wetting agents and the like.

The polyethylenimine and polyvinylamine crystallization inhibitors of the present invention may include one or more of a polyethylenimine or a polyvinylamine and co-polymers, derivatives and mixtures thereof.

The polyethylenimines described herein may include any linear or branched-chain polyethylenimine polymer or oligomer comprised of 4 or more monomer units, and derivatives, analogs, co-polymers and mixtures thereof. Preferred polyethylenimine crystallization inhibitors may include, for example, Lupasol® G20, Lupasol® FG, Lupasol® G35, Lupasol® P and Lupasol® 1595 (Lupasol is a registered trademark of BASF Aktiengesellschaft), Epomin SP-003, Epomin SP-006, Epomin SP-012, Epomin SP-018, Epomin SP-200, Epomin SP-1000 and Epomin SP-1050 (Epomin is a registered trademark of Nippon Shokubai), tetraethylenepentamine and copolymers of polyethylenimines and poly(ethylene glycol).

The polyvinylamines described herein may include linear polyvinylamines, cationic and anionic polyvinylamine copolymers and charged or protonated polyvinylamines. The linear polyvinylamines may include one or more of the Lupamin® family of products such as Lupamin® 1595, Lupamin® 4500, Lupamin® 5095, Lupamin® 9030, Lupamin® 9050 and Lupamin® 9095. The cationic and anionic polyvinylamine copolymers may include one or more of the Luredur® family of products, such as Luredur® Am na, Luredur® AV, Luredur® VH, Luredur® VI, Luredur® VM, Luredur® PR8094, Luredur® PR8261 and Luredur® PR8349. The charged or protonated polyvinylamines may include one or more of the Catiofast® family of products such as Catiofast® GM, Catiofast® PL, Catiofast® PR8236, Catiofast® VCB, Catiofast® VFH, Catiofast® VLW, Catiofast® VMP and Catiofast® VSH. (Lupamin®, Luredur® and Catiofast® are registered trademarks of BASF Aktiengesellschaft).

The polyethylenimine or polyvinylamine crystallization inhibitors of the present invention may comprise, with respect to the compatible aqueous herbicide solution, from about 0.001 to about 5 weight percent, preferably from about 0.01 to about 2 weight percent, and more preferably from about 0.01 to about 0.5 weight percent.

The present invention concerns a method of improving the compatibility of an aqueous herbicide solution which may be either a concentrate or a spray solution prepared by diluting such a concentrate or by tank mixing the components of the spray solution. The aqueous herbicide concentrate may comprise the use of, with respect to the total composition, from about 0.05 to about 10 weight percent, preferably from about 0.1 to about 5 weight percent of one or more polyethylenimine or polyvinylamine crystallization inhibitors and from about 20 to about 60 weight percent on an acid equivalent basis of a water soluble salt of 2,4-D or a water soluble salt of glyphosate, or a pre-mix concentrate containing the water soluble salts of 2,4-D and glyphosate. The aqueous herbicide concentrate of improved compatibility is preferably a solution containing the polyethylenimine or polyvinylamine crystallization inhibitor dissolved in the concentrate which upon dilution in water with products or solutions and at conditions that are normally prone to cause incompatibility, as described herein, forms an herbicide spray solution of improved compatibility. The herbicide spray solution of improved compatibility may also be prepared by tank mixing the individual components of the spray solution at the point of use. Such a spray solution may also be combined with or diluted with products or solutions and at conditions that are normally prone to cause incompatibility, as described herein, to form an herbicide spray solution of improved compatibility.

The current invention has utility at lower pH than the cited art approaches. Use of polyethylenimine or polyvinylamine crystallization inhibitors in aqueous spray solutions containing soluble salts of 2,4-D and glyphosate, and inorganic cations provides solutions of improved compatibility at pH levels as low as about 4.5. This method offers the advantage of providing herbicide spray compositions at the lower pH level where the herbicide active ingredients may be more biologically active without the need to raise the pH above about 6.5 to achieve compatibility.

In a typical procedure for preparing a compatible aqueous spray solution containing the water soluble salts of glyphosate and 2,4-D, the aqueous soluble concentrates of the salts of glyphosate and 2,4-D are added to an aqueous solution containing the polyethylenimine or polyvinylamine crystallization inhibitor. In addition, other co-formulation ingredients such as water soluble or water dispersible ingredients including, but not limited to, dispersing agents, wetting agents, spray drift reduction agents and antifoam agents, may optionally be added to the spray solution with good mixing.

An example of a method for improving the compatibility of a spray solution at a pH below about 6.5 containing the water soluble salts of glyphosate and 2,4-D, and inorganic cations comprises:
  a) preparing a solution in water comprising, with respect to the final spray solution, from about 0.01 to about 2 weight percent of Lupasol® G35 (Lupasol is a registered trademark of BASF Aktiengesellschaft);
  b) adding an aqueous concentrate of 2,4-D DMA to the solution prepared in a) to provide a solution comprising, with respect to the final spray solution, from about 0.3 to about 5 weight percent of 2,4-D on an acid equivalent (ae) basis;
  c) adding an aqueous concentrate of Roundup Weather-Max® herbicide (registered trademark of Monsanto; aqueous concentrate containing glyphosate potassium salt) to the solution prepared in b) to provide a solution comprising, with respect to the final spray solution, from about 0.5 to about 5 weight percent of glyphosate on an acid equivalent (ae) basis where the final pH is preferably less than about 6.5;
  d) adding an aqueous solution of ammonium sulfate (AMS) to the solution prepared in c) to give a solution comprising, with respect to the final spray solution, of about 2 weight percent of AMS; and
  d) optionally, adding other inert co-formulation ingredients to the solution prepared in d).

The above spray solution of improved compatibility can easily be prepared by one of ordinary skill in the art.

Another embodiment of the present invention concerns a composition wherein the aqueous herbicide solution of improved compatibility is a spray solution. The aqueous herbicide spray solution may be prepared by diluting one or more aqueous herbicide concentrates or by tank mixing the components of the spray solution. Such a spray solution may comprise, with respect to the total spray solution, from about 0.001 to about 5 weight percent, preferably from about 0.01 to about 2 weight percent and more preferably from about 0.01 to about 0.5 weight percent of one or more polyethylenimine or polyvinylamine crystallization inhibitors, from about 0.3 to about 10 weight percent, preferably from about 0.3 to about 5 weight percent each of a water soluble salt of 2,4-D and a water soluble salt of glyphosate and optionally, any additional ingredients with the proviso that at least one of the components or additional ingredients of the solution contains inorganic cations.

Another embodiment of the present invention concerns an aqueous herbicide concentrate which contains one or more polyethylenimine or polyvinylamine crystallization inhibitors and a water soluble salt of 2,4-D or glyphosate, or a pre-mix containing water soluble salts of 2,4-D and glyphosate. The concentrate may comprise, with respect to the total composition, from about 0.05 to about 10 weight percent, preferably from about 0.1 to about 5 weight percent of one or more polyethylenimine or polyvinylamine crystallization inhibitors, and from about 20 to about 60 weight percent on an acid equivalent basis of at least one of a water soluble salt of 2,4-D and a water soluble salt of glyphosate. The aqueous herbicide concentrate is preferably a solution containing the polyethylenimine or polyvinylamine crystallization inhibitor dissolved in the concentrate which upon dilution in water with products or solutions and at conditions that are normally prone to cause incompatibility, as described herein, forms an herbicide spray solution of improved compatibility.

In a typical method for preparing the aqueous herbicide concentrate, the one or more polyethylenimine or polyvinylamine crystallization inhibitors, the water soluble salt of at least one of 2,4-D and glyphosate, and optionally, any additional ingredients, are mixed together in water to provide the aqueous concentrate. The order of addition of ingredients and the mixing conditions can easily be determined by one of ordinary skill in the art.

The present invention also concerns a dry herbicide composition which comprises, with respect to the total composition, from about 0.05 to about 10 weight percent, preferably from about 0.1 to about 5 weight percent of one or more polyethylenimine or polyvinylamine crystallization inhibitors and from about 20 to about 80 weight percent on an acid equivalent basis of a water soluble salt of 2,4-D or a water soluble salt of glyphosate, or a mixture of water soluble salts of 2,4-D and glyphosate. The dry composition forms an herbicide spray solution of improved compatibility upon dissolution in water with products or solutions and at conditions that are normally prone to cause incompatibility, as described herein.

In a typical method for preparing the dry herbicide composition, the one or more polyethylenimine or polyvinylamine crystallization inhibitors, the water soluble salt of at least one of 2,4-D and glyphosate, and optionally, any additional ingredients, are mixed together in water to provide an aqueous concentrate. The order of addition of ingredients and the mixing conditions used can easily be determined by one of ordinary skill in the art. The aqueous concentrate may then be concentrated by removal of water and then dried to provide the dry herbicide composition which may also be prepared by dry blending the ingredients described herein. The dry composition can be added to an aqueous spray solution containing products or solutions and at conditions that are normally prone to cause incompatibility, as described herein, to form a compatible herbicide spray solution. It is commonly known that concentrated or dry formulations may be diluted or dissolved in water at from about 10 to about 500 fold at the point of use depending on the agricultural practices.

A further embodiment of the present invention concerns a method of using the aqueous herbicidal spray solution of improved compatibility for agricultural spray applications such as for the control of undesired plant growth. The herbicidal spray solution of improved compatibility containing the active ingredients at herbicidally effective concentrations may be used to treat undesired plant growth.

The effective amount of the active ingredients of the present invention to be employed in a typical agricultural application often depends upon, for example, the type of plants, the stage of growth of the plant, severity of environmental conditions, the weeds to be controlled and application conditions. Typically, a weed plant in need of control is contacted with an amount of the aqueous herbicidal spray solution that will provide an amount from about 1 to about 40,000 parts per million (ppm), preferably from about 10 to about 20,000 ppm of the active ingredient. The contacting may be in any effective manner. For example, any exposed part of the plant, e.g., leaves or stems may be sprayed with the active ingredient as a solution in a carrier such as water.

The aqueous herbicidal spray solution of improved compatibility is especially useful for the control of weeds in crops that are naturally tolerant to or have been made tolerant to or resistant to the herbicides contained in the spray solution by genetic manipulation or by mutation and selection. For example, corn, wheat, rice, soybean, sugar beet, cotton, canola, and other crops that have been made tolerant to or resistant to glyphosate and are naturally tolerant or resistant to or have been made genetically tolerant or resistant to 2,4-D can be treated. The aqueous herbicidal spray solutions of the present invention are also effective in controlling many weeds that have become resistant to glyphosate, for example, horseweed (*Conyza canadensis*, ERICA).

Optionally, the compositions of the present invention may contain a surfactant. The surfactants can be anionic, cationic or nonionic in character. Typical surfactants include salts of alkyl sulfates, such as diethanolammonium lauryl sulfate; alkylarylsulfonate salts, such as calcium dodecylbenzenesulfonate; alkyl and/or arylalkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; ethoxylated amines, such as tallowamine ethoxylated; betaine surfactants, such as cocoamidopropyl betaine; polyethylene glycol esters of fatty acids, such as polyethylene glycol stearate; block copolymers of ethylene oxide and propylene oxide; salts of mono and dialkyl phosphate esters; and mixtures thereof. The amounts and combinations of these surfactants to be used can easily be determined by one of ordinary skill in the art. It may be advantageous to avoid the use of surfactants that contain inorganic ions such as, for example, Na, K, NH4 in order to maintain the physical stability of the compositions of the present invention.

In addition to the compositions set forth above, the present invention also may include compositions containing one or more additional compatible ingredients. These additional ingredients may include, for example, one or more pesticides or other ingredients, which may be dissolved or dispersed in the composition and may be selected from acaricides, algicides, antifeedants, avicides, bactericides, bird repellents, chemosterilants, defoliants, desiccants, disinfectants, fungicides, herbicide safeners, herbicides, insect attractants, insecticides, insect repellents, mammal repellents, mating disrupters, molluscicides, plant activators, modifiers of plant size and structure, rodenticides, semiochemicals, synergists and virucides. Also, any other additional ingredients providing functional utility such as, for example, antifoam agents, antimicrobial agents, buffers, corrosion inhibitors, dispersing agents, dyes, fragrants, freezing point depressants, neutralizing agents, odorants, penetration aids, sequestering agents, spreading agents, stabilizers, sticking agents, viscosity-modifying additives and the like, may be included in these compositions.

The following examples illustrate the present invention.

Example 1

Reduction of the On-Set pH of Crystallization of 2,4-D Potassium With Added Polyethylenimine or Polyvinylamine Crystal Inhibitors (CI)

The on-set pH of crystallization (the pH of the solution when crystallization begins) of a 100 mL sample of an aqueous solution of 3 weight percent (acid equivalent basis) of 2,4-D potassium (2,4-D K) with and without added polyethylenimine or polyvinylamine crystal inhibitors (CI) was determined as the pH was slowly lowered by the addition of 0.2 N aqueous sulfuric acid. As shown in Table 1, the addition of from 0.1 to 0.2 weight percent of the CI, with respect to total solution, to the aqueous solution of 2,4-D K significantly reduced the on-set pH of crystallization of 2,4-D K as compared to the control example where no CI was used.

TABLE 1

Inhibition of 2,4-D Potassium Salt Crystallization from Aqueous Solutions at Low pH With Polyethylenimine or Polyvinylamine Crystal Inhibitors (CI)

| 2,4-D K Salt wt % ae | CI Added[1] | CI wt % | On-set pH of Crystallization |
|---|---|---|---|
| 3% | none (control) | 0 | 6.15 |
| 3% | Lupasol ® G20 | 0.2% | 4.13 |
| 3% | Lupasol ® FG | 0.2% | 3.92 |
| 3% | Lupasol ® G35 | 0.1% | 5.06 |
| 3% | Lupasol ® P | 0.2% | 5.16 |
| 3% | TEPA | 0.2% | 5.68 |
| 3% | Lupamine ® 1595 | 0.2% | 5.12 |
| 3% | 80% ethoxylated PEI[2] | 0.2% | 4.86 |

[1]TEPA = tetraethylenepentamine; Lupasol ® and Lupamine ® are registered trademarks of BASF Aktiengesellschaft;
[2]Polyethylenimine, 80% ethoxylated (Sigma-Aldrich)

Example 2

Spray Solution Compatibility of Salts of 2,4-D and Glyphosate With Added Crystal Inhibitor (CI)

Spray solutions were formed from aqueous concentrates of 2,4-D choline (prepared by mixing equimolar amounts of 2,4-D acid and choline hydroxide in water) or 2,4-D DMA and various glyphosate salts (potassium, isopropyl ammonium or dimethyl ammonium) at various concentrations (weight percent acid equivalent basis) of the respective active ingredients with and without added polyethylenimine or polyvinylamine crystal inhibitor (CI). As shown in Table 2, the addition of CI to the spray solutions containing the soluble salts of 2,4-D and glyphosate in the presence of 2% ammonium sulfate (AMS) significantly reduced or eliminated the formation of crystals when compared to the respective controls where no CI was used.

TABLE 2

Compatibility of Spray Solutions Containing 2,4-D and Glyphosate Salts, and 2% AMS With and Without Added Crystal Inhibitor (CI) After 24 Hours At Room Temperature[1]

| 2,4-D Salt | Glyphosate Salt[2] | 2,4-D wt % ae | Glyphosate wt % ae | Crystal Inhibitor (CI) Added[3] | CI wt % in Tank Mixture | Result[4] |
|---|---|---|---|---|---|---|
| choline | WeatherMax ® | 1.71 | 1.8 | none | 0 | 3 |
| choline | WeatherMax ® | 0.95 | 1.0 | none | 0 | 3 |
| choline | WeatherMax ® | 1.8 | 1.8 | TEPA | 0.1% | 3 |
| choline | WeatherMax ® | 1.8 | 1.8 | TEPA | 0.2% | 1 |
| choline | WeatherMax ® | 1.8 | 1.8 | TEPA | 0.4% | 0 |
| DMA | Gly Star ® Plus | 1.7 | 1.8 | Lupasol ® G20 | 0.1% | 0 |
| DMA | Durango ® DMA ® | 1.7 | 1.8 | Lupasol ® G20 | 0.1% | 0 |
| choline | WeatherMax ® | 1.8 | 1.8 | Lupasol ® G20 | 0.1% | 0 |
| choline | WeatherMax ® | 2.4 | 2.4 | Lupasol ® G20 | 0.1% | 1 |
| choline | WeatherMax ® | 1.8 | 1.8 | Lupasol ® G35 | 0.1% | 0 |
| choline | WeatherMax ® | 1.8 | 1.8 | Lupasol ® P | 0.1% | 0 |

[1]Water with a hardness of 342 ppm was used to make all spray solutions
[2]WeatherMax ® = Roundup WeatherMax ® herbicide (registered trademark of Monsanto) is an aqueous concentrate containing glyphosate potassium; Gly Star ® Plus herbicide (registered trademark of Albaugh, Inc.) is an aqueous concentrate containing glyphosate isopropyl ammonium; Durango ® DMA ® herbicide (registered trademark of Dow AgroSciences LLC) is an aqueous concentrate containing glyphosate dimethyl ammonium (DMA)
[3]TEPA = tetraethylenepentamine; Lupasol ® is a registered trademark of BASF Aktiengesellschaft
[4]Observation 24 hours after preparation of the simulated tank mixture: 0 = no crystals, 1 = trace amount of crystals, 2 = moderate amount of crystals, 3 = large amount of crystals Example 3

Preparation of a Compatible Aqueous Concentrate of 2,4-D Choline Salt and Dilution of it in Spray Solutions Containing Glyphosate Salts and AMS To prepare 20 g of a 2,4-D choline salt formulation with a concentration of 456 g acid equivalent per liter and containing 1% (w/w) of a CI, e.g. Lupasol® G20 (Lupasol® is a registered trademark of BASF Aktiengesellschaft), 7.7 g of 2,4-D acid technical (purity 97%) was mixed with 0.4 g of a Lupasol® G20 solution (50% in water) and 7.2 g of a choline hydroxide solution (45% choline hydroxide in water). Once the 2,4-D acid was completely dissolved, 0.66 g of ethylenediaminetetraacetic acid mono-choline salt (25.4% in water) was mixed into the clear solution. An additional 1-1.4 g of the choline hydroxide solution were then added to adjust the pH value of the concentrate to about 7.0 and water was added to provide a final sample weight of 20 g. Addition of this concentrate to spray solutions containing glyphosate potassium or glyphosate DMA salts and 2% AMS provided spray solutions of improved compatibility as indicated in Table 3.

TABLE 3

Compatibility of Spray Solutions Prepared by Mixing the 456 g ae/L Aqueous Concentrate of 2,4-D Choline Salt Containing 1% Lupasol ® G20 with Spray Solutions of Glyphosate Potassium or DMA Salts and 2% AMS After 24 Hours At Room Temperature[1]

| 2,4-D Salt | Glyphosate Salt[2] | 2,4-D wt % ae | Glyphosate wt % ae | Result[3] |
|---|---|---|---|---|
| choline | WeatherMax ® | 1.7 | 1.8 | 0 |
| choline | WeatherMax ® | 0.86 | 0.90 | 0 |
| choline | WeatherMax ® | 0.57 | 0.60 | 0 |
| choline | Durango ® DMA | 1.7 | 1.8 | 0 |

TABLE 3-continued Compatibility of Spray Solutions Prepared by Mixing the 456 g ae/L Aqueous Concentrate of 2,4-D Choline Salt Containing 1% Lupasol ® G20 with Spray Solutions of Glyphosate Potassium or DMA Salts and 2% AMS After 24 Hours At Room Temperature[1]

| 2,4-D Salt | Glyphosate Salt[2] | 2,4-D wt % ae | Glyphosate wt % ae | Result[3] |
|---|---|---|---|---|
| choline | Durango ® DMA | 0.86 | 0.90 | 0 |
| choline | Durango ® DMA | 0.57 | 0.60 | 0 |

[1]Water with a hardness of 342 ppm was used to make all spray solutions; Lupasol ® is a registered trademark of BASF Aktiengesellschaft
[2]WeatherMax ® = Roundup WeatherMax ® herbicide (registered trademark of Monsanto) is an aqueous concentrate containing glyphosate potassium; Durango ® DMA ® herbicide (registered trademarks of Dow AgroSciences LLC) is an aqueous concentrate containing glyphosate dimethyl ammonium (DMA)
[3]Observation 24 hours after preparation of the simulated tank mixture: 0 = no crystals, 1 = trace amount of crystals, 2 = moderate amount of crystals, 3 = large amount of crystals

What is claimed is:

1. A method of improving the compatibility of aqueous herbicide solutions containing a water soluble salt of 2,4-D and a water soluble salt of glyphosate, wherein the solutions contain one or more inorganic cations selected from the group consisting of $NH_4^+$, $Na^+$, $K^+$, $Ca^{2+}$, $Mg^{2+}$, $Fe^{2+}$, $Fe^{3+}$, $Cu^{2+}$, $Mn^{2+}$ and $Zn^{2+}$, which comprises adding to the aqueous herbicide solution one or more polyethylenimine or polyvinylamine crystallization inhibitors, wherein the pH of the aqueous herbicide solution is below or about 6.5, the weight percent ratio of 2,4-D to glyphosate on an acid equivalent basis is from about 16:1 to about 1:16, and the crystallization inhibitor is added in an amount sufficient to improve compatibility and reduce the amount of solids formed.

2. An aqueous herbicide solution of improved compatibility containing one or more inorganic cations selected from the group consisting of $NH_4^+$, $Na^+$, $K^+$, $Ca^{2+}$, $Mg^{2+}$, $Fe^{2+}$, $Fe^{3+}$, $Cu^{2+}$, $Mn^{2+}$ and $Zn^{2+}$ comprising water soluble salts of both 2,4-D and glyphosate, and one or more polyethylenimine or polyvinylamine crystallization inhibitor, wherein the pH of the aqueous herbicide solution is below or about 6.5, the weight percent ratio of 2,4-D to glyphosate on an acid equivalent basis is from about 16:1 to about 1:16, and the crystallization inhibitor is added in an amount sufficient to improve compatibility and reduce the amount of solids formed.

3. The aqueous herbicide solution of claim 2 which is a concentrate.

4. The aqueous herbicide concentrate of claim 3 in which the polyethylenimine or polyvinylamine crystallization inhibitor is from about 0.05 to about 10 weight percent of the concentrate.

5. The aqueous herbicide solution of claim 2 which is a spray solution.

6. The aqueous herbicide spray solution of claim 5 in which the polyethylenimine or polyvinylamine crystal inhibitor is from about 0.001 to about 5 weight percent of the spray isolation.

7. The aqueous herbicide solution of claim 2 in which the weight percent ratio of 2,4-D to glyphosate on an acid equivalent basis is from about 10:1 to about 1:1.

8. The aqueous herbicide solution of claim 2 in which the weight percent ratio of 2,4-D to glyphosate on an acid equivalent basis is from about 1:1 to about 1:16.

9. A dry herbicide composition comprising one or more polyethylenimine or polyvinylamine crystallization inhibitors, a water soluble salt of 2,4-D or glyphosate, or and a mixture of water soluble salts of 2,4-D and glyphosate, wherein the dry herbicide composition is added to an aqueous herbicidal solution with a pH below or about 6.5, the weight percent ratio of 2,4-D to glyphosate on an acid equivalent basis in the aqueous herbicidal solution is from about 16:1 to about 1:16, and the one or more crystallization inhibitors are added in an amount sufficient to improve compatibility and reduce the amount of solids formed in the aqueous herbicidal solution.

10. The dry herbicide composition of claim 9 in which the polyethylenimine or polyvinylamine crystallization inhibitor is from about 0.05 to about 10 weight percent of the composition.

* * * * *